United States Patent [19]

Small

[11] Patent Number: 4,917,604
[45] Date of Patent: Apr. 17, 1990

[54] COMPRESSION STAPLE, METHOD AND APPARATUS FOR INSERTION OF SAME

[76] Inventor: Irwin A. Small, 6861 Orinoco Cir., Birmingham, Mich. 48010

[21] Appl. No.: 184,088

[22] Filed: Apr. 20, 1988

[51] Int. Cl.⁴ .............................................. A61C 8/00
[52] U.S. Cl. ..................................... 433/174; 433/173
[58] Field of Search ............................ 433/173, 174; 128/92 VY, 92 VD, 92 YC

[56] References Cited

U.S. PATENT DOCUMENTS

| | | | |
|---|---|---|---|
| Re. 28,841 | 6/1976 | Allgower et al. | 128/92 D |
| 3,414,975 | 12/1968 | Small | 32/2 |
| 3,664,022 | 5/1972 | Small | 32/2 |
| 3,704,707 | 12/1972 | Halloran | 128/92 EB |
| 3,748,739 | 7/1973 | Thibert | 32/10 A |
| 3,782,373 | 1/1974 | Smythe | 128/92 EB |
| 3,895,444 | 7/1975 | Small | 32/10 A |
| 4,341,206 | 7/1982 | Perrett et al. | 128/92 EB |
| 4,349,018 | 9/1982 | Chambers | 128/92 E |
| 4,364,381 | 12/1982 | Sher et al. | 128/92 E |
| 4,439,152 | 3/1984 | Small | 433/173 |
| 4,493,317 | 1/1985 | Klaue | 128/92 D |
| 4,502,475 | 3/1985 | Weigle et al. | 128/92 EB |
| 4,516,937 | 5/1985 | Bosker | 433/173 |
| 4,522,201 | 6/1985 | Tongue | 128/92 EB |
| 4,599,999 | 7/1986 | Klaue | 128/92 E |
| 4,608,972 | 9/1986 | Small | 128/92 EB |

FOREIGN PATENT DOCUMENTS 882466 7/1951 Fed. Rep. of Germany .
770696 3/1957 United Kingdom .

OTHER PUBLICATIONS

Irwin Small, Metal Implants and the Mandibular Staple Bone Plate; Oral Surgery, vol. 33, Aug., 1975.
Irwin A. Small, Use of the Mandibular Staple Bone Plate in the Deformed Mandible; Oral Surgery, vol. 37, 1979, pp. 26-30.
Hans Boskar; The Transmandibular Implant; Sep., 1983.
Core-Vent Corp., 1987; A Hard Look at Controversies in Implantology.
Halfrick, Toph and Kaufman; Mandibular Staple Bone Plate, Long Term Evaluation of 250 Cases; JADA, vol. 104; Mar., 1982.
A. N. Cranin & T. A. Dennison, Anterior Vertical Transosteal Implant; Oral Implantology, vol. One; 17: 1970.

Primary Examiner—Robert P. Swiatek
Assistant Examiner—Nicholas D. Lucchesi
Attorney, Agent, or Firm—Gifford, Groh, Sprinkle, Patmore and Anderson

[57] ABSTRACT

A staple which is compressively affixed to the mandibular jaw with lag screws, a drill guide apparatus having a plane guide and drilling barrel for proper alignment of the staple and a method for proper implantation of the staple. The staple is provided with a plurality of parallel transosteal pins which are mounted on a mounting axis which extends in a direction parallel to the axis of compression. The plane guide has a curvilinear aperture to extend around the jaw bone for forming a planar mating surface on the bone with a grinding tool. The drilling barrel accepts a plurality of removable sleeves for guiding drill bits of different sizes. A sleeve nut is mounted on each transosteal pin of the staple to accept a dental prosthesis. A sleeve portion of the sleeve nut extends through the gingiva to reduce irritation.

15 Claims, 4 Drawing Sheets

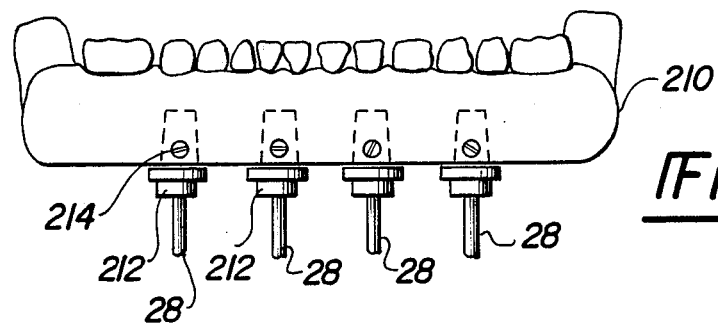
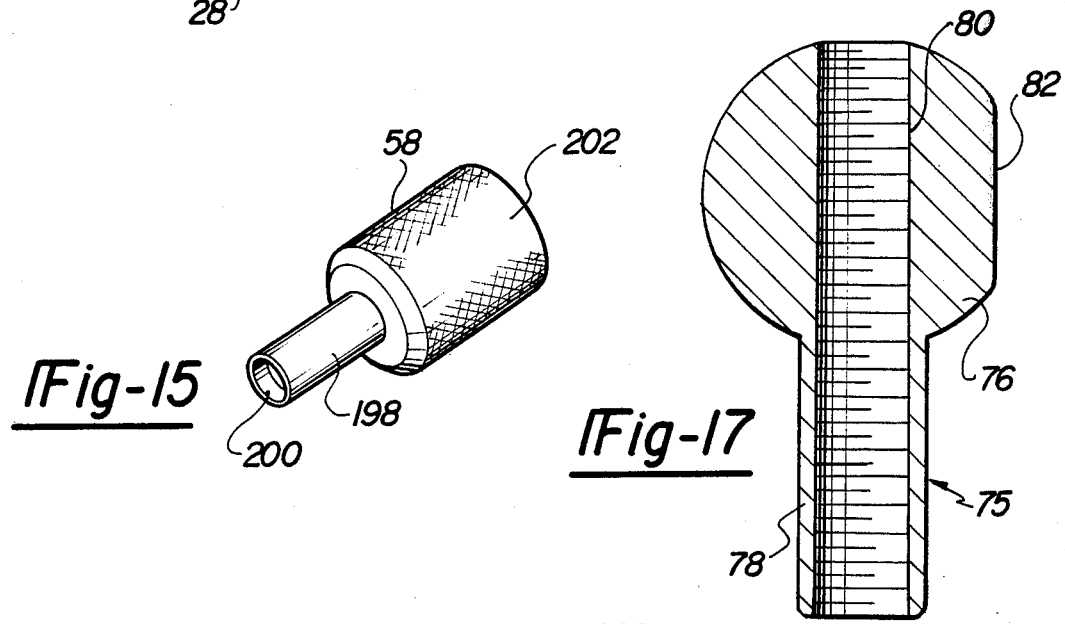
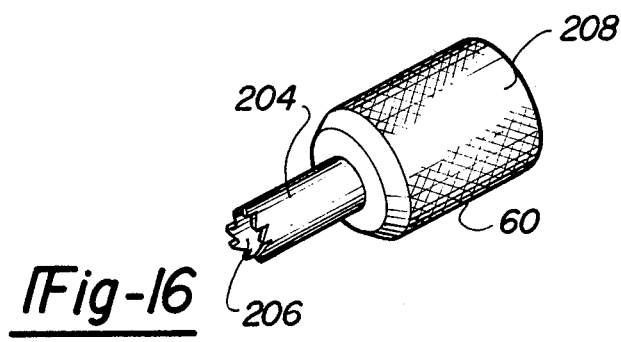

COMPRESSION STAPLE, METHOD AND APPARATUS FOR INSERTION OF SAME

BACKGROUND OF THE INVENTION

I. Field of the Invention

The present invention relates generally to a construction of a staple for compressive implantation into the mandibular jaw, a drill guide assembly for use during implantation, and a method for insertion of the staple utilizing the drill guide assembly.

II. Description of the Prior Art

Mandibular staples such as disclosed in Applicant's prior patents, U.S. Pat. Nos. 3,414,975, 3,664,022 and 3,895,444, are known for implantation in a mandible or lower jaw. The mandibular staple has been implanted for rehabilitation of various types of mandibular deformities. These deformities, which occur through aging or wasting away of bone tissue, prevent the anchoring of a dental appliance against accidental dislodgement. The mandibular staple is implanted to provide additional support against dislodgement of the dental appliance or prosthesis.

Applicant's prior staple, such as disclosed in U.S. Pat. No. 3,895,444, features a curvilinear support plate, a pair of threaded transosteal pins and a plurality of mushroom shaped fasteners. The shape of the support plate conforms to the curvilinear shape of the front end of the jaw bone. The pair of threaded transosteal pins extend outwardly from the support plate to extend through the jaw bone to receive threaded support nuts. The plurality of mushroom shaped fasteners extend upwardly from the plate for insertion into holes drilled in the jaw bone for securing the staple to the jaw bone. The staple is secured to the jaw bone when the penetrated subcutaneous tissue and bone surrounding the pins and mushroom shaped fasteners grows outwardly. The tissue eventually grows into a porous bioceramic coating on the staple to homogeneously lock the staple to the jaw bone. A dental appliance may be removably affixed to the support nuts.

Applicant's prior U.S. Pat. No. 3,664,022 featured a drill guide having a jig bore adapted for abutment with the jaw bone and a yoke member having a pair of spaced apart guide pins. The jig bore is movable on a post to abut the curved front end of the jaw bone to permit the drilling of a plurality of throughbores and blind bores in the mandibular jaw bone, for accepting the pair of pins and the plurality of mushroom shaped fasteners of the staple. The guide pins of the yoke extend to contact a template extending over the upper surface of the jaw.

Applicant's prior staple provides support for retaining a removable prosthesis or appliance. However, the prior drill guide and method of insertion provide an alignment of the transosteal pins of the staple which is substantially angled with respect to a lateral plane of the dental prosthesis and an axis of compression of the jaws. Thus, the dental prothesis is required to accept the staple at an angle to the lateral plane. Formation of the dental prosthesis in this manner is both time consuming and expensive.

Additionally, the prior staple is secured primarily by bone which grows outwardly from the holes to engage the threaded pins and mushroom shaped fasteners. However, the threads of the pins irritated the gingiva. Because alignment of the staple is angled substantially with respect to the axis of compression, and because of the manner of affixation of the staple, fixed installation of a dental appliance is not possible. The staple is not satisfactorily positioned or fixed to support the compressive loads which are generated on the prosthesis during chewing and the like. The prior staple may be used as a stabilizing device for a removable prosthesis. The prior staple may not be satisfactorily used with a prosthesis until the bone grows back around the plurality of pins and fasteners of the staple.

Thus, it would be advantageous to present a staple and method of insertion which would support the compressive forces for permanent installation of a prosthesis and which could be used soon after surgery. Such a staple would permit simpler formation and installation of the prosthesis and greatly reduce the trauma associated with the implant procedure.

SUMMARY OF THE PRESENT INVENTION

In order to overcome these disadvantages, Applicant has disclosed a mandibular compression staple which is mounted to the jaw bone, a method for insertion of the staple which permits implantation of a plurality of parallel transosteal pins of the staple on a mounting axis generally parallel to the axis of compression of the jaw and normal to the lateral axis of a prosthesis, and a drill guide apparatus for use during the implantation in accordance with the method.

The mandibular compression staple has a base plate having a flat upper surface and at least two parallel transosteal pins extending in the direction normal to the upper surface of the base plate.

The flat upper surface is abuttingly mounted to a flat mating surface formed on an underside portion of the jaw bone. The mating surface is formed normal to the mounting axis, such that the transosteal pins extend through throughbores formed in the jaw bone.

A plurality of circular bores extend through the base plate to accept a like plurality of threaded lag screws for compressively mounting the staple to the jaw bone. A nut is threaded onto each of the transosteal pins. Each nut has a sleeve portion positioned to extend downwardly through the gingiva to abut against an upper surface of the bone. The sleeve portion prevents inflamation and irritation of the gingiva caused by contact with the threads of the transosteal pin.

A drill guide assembly having a post which removably and adjustably supports a plane guide and a drilling chamber is used to facilitate implantation of the compression staple. The yoke has two pairs of mounting pins for supporting a pair of director rods. The pair of director rods extend in the direction of the drilling chamber. The director rods are mounted to one or the other of the two pairs of mounting pins to engage a template formed over the upper portion of the jaw to avoid contact with a drill bit during drilling.

The mounting axis for the mandibular staple is determined by positioning the director rods in the template and moving the drilling chamber into a position below the inferior border or under-surface of the jaw. The mounting axis is selected to extend as close to parallel with the axis of compression of the jaw and normal to the lateral axis of the prosthesis as permitted by the shape of the jaw bone.

The plane guide has a loop portion forming a curvilinear shaped aperture. The loop portion has a flat guide surface extending between a pair of ends. Once the mounting axis has been determined, the plane guide is used to form the mating surface on the inferior border. The loop portion of the plane guide is positioned over the protruding portion of the lower jaw. Any excess bone extending through the aperture beyond the guide surface is ground away with a burring tool. The burring tool has a smooth tip portion to cooperate with the guide surface to facilitate the formation of the mating surface on the inferior border of the jaw for mating with the upper surface of the compression staple. The mounting axis thus determined is properly aligned with the axis of compression.

After the mating surface has been prepared on the inferior border, the drilling chamber having teeth extending along the edge of a curvilinear top surface is mounted on the post of the drill guide assembly. The teeth of the drilling chamber lockingly engage the jaw bone to lock the drilling chamber in position for drilling. In the event the teeth prevent the top surface of the drilling chamber from engaging the flat surface of the jaw bone, a notch is ground on the inferior border to accept the teeth. The drilling chamber acts as a jig bore for forming a plurality of throughbores and a plurality of blind bores in the mandibular jaw. Both the plurality of throughbores and blind bores extend normal to the mating surface formed on the inferior border to extend in a parallel alignment with the mounting axis. The plurality of throughbores is formed to accept the transosteal pins of the compression staple and the plurality of blind bores is formed to accept the plurality of lag screws. A first plurality of sleeves, each having first predetermined diameters corresponding to the drill bits used for forming the throughbores, and a second plurality of sleeves, each having a second predetermined diameter, are removably mounted to the drilling chamber.

Applicant further discloses a gingival cutter and a bone crest leveler for use in forming a cavity through the gingiva and leveling the surface of the top of the bone to receive the sleeve of the nut mounted to each transosteal pin.

Applicant's method of implantation includes determining a mounting axis for the mandibular staple generally parallel to an axis of compression of the lower jaw, grinding a mating surface normal to the mounting axis, forming grooves in the jaw bone adjacent to the mating surface, locking the teeth of the drilling chamber in the grooves for drilling the jaw bone and compressing the upper surface of the staple against the mating surface of the jaw with self-tapping lag screws.

Thus, Applicant has disclosed a method and apparatus for insertion of a mandibular staple which provides for alignment of the mounting axis of the staple generally parallel to the compressive axis of the patient's lower mandibular jaw. Additionally, the staple is compressively mounted to the mandibular jaw to provide a base for vertical loading to permit the mounting of a fixed prosthesis. The transosteal pins are, thus, maintained in parallel spaced apart relationship and aligned generally normal to the lateral plane of the prosthesis to further facilitate in the production and mounting of the prosthesis.

Applicant's plane guide provides a template for creating a planar mating surface on the jaw bone. The drilling chamber has a plurality of teeth to lock the drill guide in position in grooves formed in the jaw bone to prevent wandering of a drill bit during the drilling operation and to improve the alignment of the holes formed for the staple, thus facilitating the insertion of the staple into the jaw.

These and many other advantages of Applicant's method and apparatus and for use with a fixed mandibular staple will be apparent to those skilled in the art.

BRIEF DESCRIPTION OF THE DRAWINGS

FIG. 14 is a perspective view of a prosthesis in position upon the transosteal pins of a compression staple;

FIG. 15 is a perspective view of the gingival cutter;

FIG. 16 is a perspective view of a bone crest leveler; and

FIG. 17 is a perspective view of an alternative embodiment of a sleeve nut mounted on a transosteal pin.

DESCRIPTION OF THE PREFERRED EMBODIMENT

Figure 1:
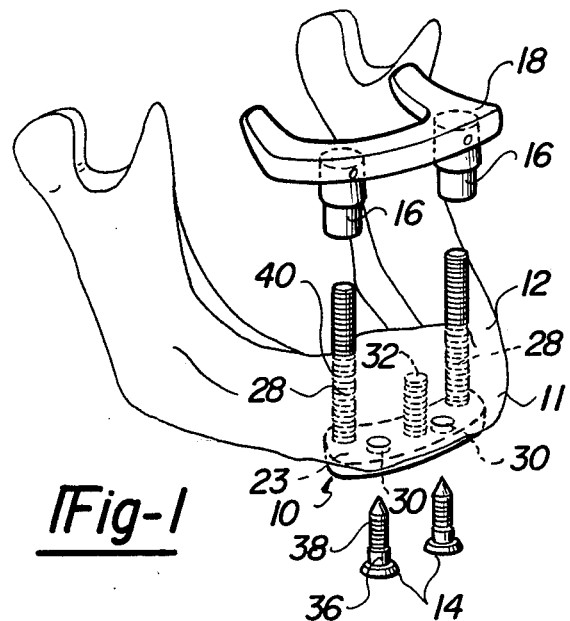
FIG. 1 is an exploded view of a mandibular jaw with a two transosteal pin staple, sleeve nuts and a prosthesis.
Figure 2:
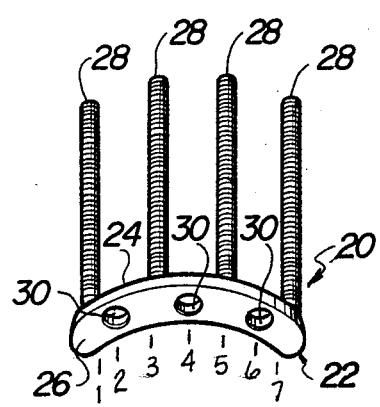
FIG. 2 is a perspective view of a four transosteal pin staple according to the invention.

With reference to the drawings, a compression staple according to the invention is shown in two sizes in FIGS. 1 and 2. A smaller two transosteal pin compression staple is shown in FIG. 2. A four transosteal pin compression staple 20 according to the invention is shown in FIG. 2. In FIG. 1, the two transosteal pin staple 10 is shown implanted through a mandibular jaw 12. The staple 10 is secured compressively in position by two self-tapping lag screws 14. Sleeve nuts 16 are threaded on each transosteal pin 28 to provide support for a bridge structure 18 to which a prosthesis may be affixed. The two transosteal pin staple is suitable for use in the jaws of adolescents and smaller adults.

Figure 9:
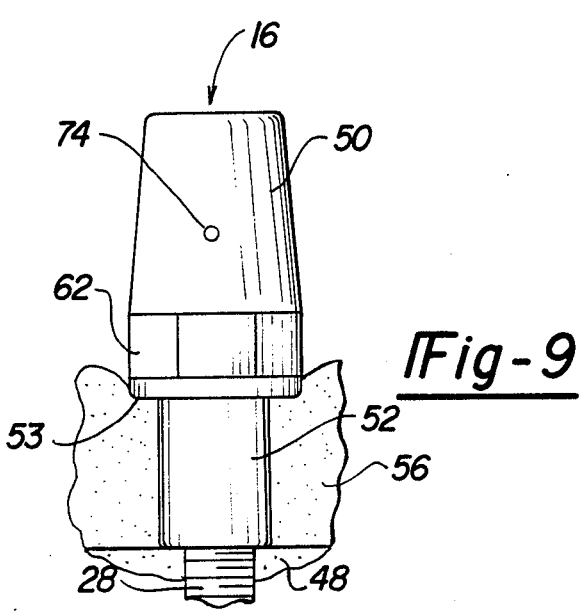
FIG. 9 is a side view of a sleeve nut mounted in position on a transosteal pin.

The four transosteal pin staple 20 shown in FIG. 2 has a curvilinear shaped base plate 22 having a flat upper surface 24 and a flat bottom surface 26. Each of four transosteal pins 28 is mounted to extend upwardly in a direction normal to the plane of the upper surface 24 of the base plate 22. Each transosteal pin 28 has a length greater than the combined thickness of the jaw bone and gingiva, to threadably accept a sleeve nut 16 as best shown in FIG. 9. Each transosteal pin 28 is located at positions shown at 1, 3, 5 and 7 on the base plate 22 are formed of a suitable corrosion resistant material such as a high strength titanum alloy (TIV). The transosteal pins 28 extend along parallel axes and are affixed to the base plate 22 in a suitable manner such as laser welding. The surface of the staple may be coated with a bioceramic material such as aluminum oxide hydroxylapatite to improve interaction with the bone.

Each of three circular bores 30 extend through the base plate 22 at positions 2, 4, and 6 indicated in FIG. 2, and are, thus, positioned between each pair of the four transosteal pins 28. Each of the three bores 30 is formed to accept one self-tapping lag screw 14.

Each lag screw 14 has a cylindrical portion 36 extending between a head 34 and a threaded end portion 38. The threaded end portion 38 is provided with self-tapping type threads. The head 34 is provided with an opening such as a hexagonal shaped indentation 39 for accepting a shaft of a driver such as an Allen wrench or Spline screwdriver (not shown) for threadably advancing the lag screw 14 into the jaw bone.

Figure 4:
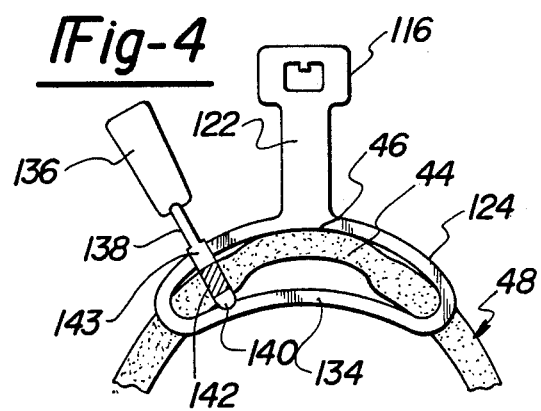
FIG. 4 is a plane view of the plane guide positioned on the inferior border of the mandibular jaw for grinding with a burring tool.

As set forth more fully below, the compression staple 10 is implanted in the mandibular jaw by inserting each transosteal pin 28 through a respective throughbore 40, as shown for the two pin staple in FIG. 1, drilled through the jaw. A flat mating surface 44 is formed on an inferior border 46 of the jaw bone 48 as shown in FIG. 4.

Figure 8:
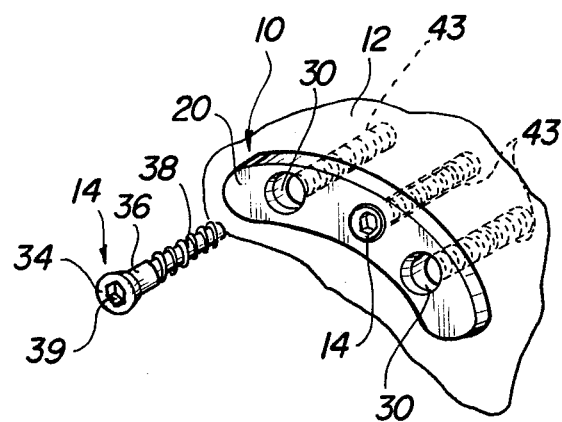
FIG. 8 is an exploded view of a staple in position in the mandibular jaw.

As shown in FIG. 8, the four pin staple 20 is inserted in the jaw so that the upper surface 23 of the base plate 22 securely abuts the mating surface 44 to prevent displacement of the staple during chewing. One lag screw 14 is then inserted through each of the three circular bores 30 in the base plate 22 and threadably driven into a plurality of blind bores 43 formed in the mandibular jaw 12 to compressively connect the staple to the jaw. Each blind bore 43 has a diameter smaller than the diameter of the lag screw 14, for instance, 2 mm, to permit self-tapping threading of the lag screw 14 in the blind bore 43. The blind bores are drilled to a predetermined depth of, for instance, 9, 12 or 15 mm, depending on the length of the lag screw 14 being used.

Figure 11:
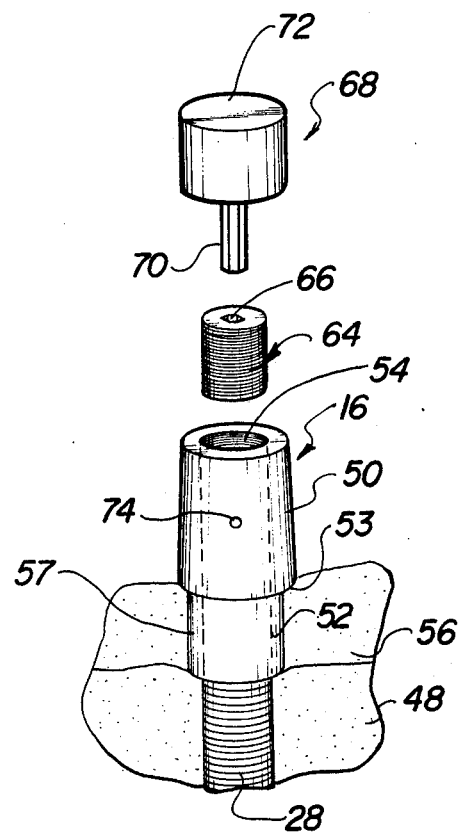
FIG. 11 is an exploded view of a nut, set screw and insertion tool.

As shown in FIG. 11, after the staple has been inserted, the sleeve nut 16 is threadably mounted on each transosteal pin 28. Each sleeve nut 16 has a frusto-conical head 50 and a sleeve portion 52 extending outwardly from the head 50. An annular surface 53 extends between the head 50 and sleeve portion 52. Flat surfaces 62 may be formed on the head 50 as shown in FIG. 9. In the preferred embodiment, six flat surfaces 62 formed in the shape of a hexagon are positioned for use with a tool such as a socket wrench for threading the sleeve nut 16 onto the transosteal pin 28. The sleeve nut has a threaded throughbore 54 for engaging the threads of the transosteal pin 28. The sleeve portion 52 has a predetermined length generally equal to the thickness of the layer of gingiva 56 extending above the bone 48 of the mandible. As will be discussed more fully below, a cavity 57 is formed through the gingiva 56 to accept the sleeve with a trephine 58, as shown in FIG. 15. If necessary, a portion of the top surface of the bone 48 is further removed with a crest leveler 60, as shown in FIG. 16. The crest leveler 60 removes bone to provide a flat surface, so that the annular surface 53 of the head of the nut contacts gingiva 56 and the end surface of the sleeve portion 52 rests firmly against the bone 48 of the jaw.

After the final position of the nut 16 has been established, the sleeve nut 16 is removed from the transosteal pin 28 and the pin shortened so as not to extend fully through the throughbore 54 of the nut 16.

As shown in FIG. 11, a threaded cylindrical plug 64 having a hexagonally shaped bore 66 extending axially is inserted into the threaded throughbore 54 at the head of the nut to contact the top of the transosteal pin 28 and lock the plug 64 and the nut 16 in position on top of the transosteal pin 28. The plug 64 is threadably advanced in the nut by turning the plug with a driving tool 68 having a hexagonally shaped finger 70 extending outwardly from a handle 72. The finger 70 is adapted to mate with the hexagonally shaped bore 66 of the plug 16. After the plug 64 is tightened against the top of the transosteal pin 28, a set screw 74 extending through the plug may be advanced radially through the nut 16 to engage the plug 66 to lock the nut and plug together. In this manner, the nut is lockingly affixed to the transosteal pin to aid in maintaining the staple (10 or 20) in position within the jaw.

An alternative embodiment of the sleeve nut is shown in FIG. 17, a nut 75 having a spherically shaped head 76 with a sleeve 78 extending outwardly from the head. A threaded throughbore 80 extends axially through the nut 75. A flat surface 82 is formed on the spherically shaped head 76 to extend parallel with the axis of the nut 75 to provide a surface for seating a set screw 214 of a denture 210 (shown in FIG. 14). The nut 75 may be locked into position on the transosteal pin 28 in the same manner as described above for the sleeve nut 16.

The four pin staple 20 is, thus, compressively implanted. The four sleeve nuts 16 affixed to the staple provide a sufficient platform for permanent fixation of a dental appliance. However, the smaller two pin staple 10 does not provide a sufficient base to support a fixed attachment of an appliance. Therefore, the four pin staple should be used whenever the jaw bone is sufficiently large to accomodate one, in order to provide a base for affixed attachment of a prosthesis.

If the arc of the jaw is too small to allow proper drilling of holes at positions 1 and 7 for the outermost transosteal pins of the four pin staple, the two pin staple should be used. A base plate 23 of the two pin staple 10 is similar to the base plate 22 of the four pin staple; however, the base plate extends only between the base plate positions 2 to 6, as indicated in FIG. 2, for the four pin staple. Positions 2 through 6 of the four pin staple have equivalent positions on the two pin staple. As shown in FIG. 1, two transosteal pins 28 are positioned at positions 2 and 6, respectively. A short threaded pin 32 is positioned at position 4. The short pin 32 does not extend through the jaw bone. Two circular apertures 30 are formed at positions 3 and 5, respectively, for the lag screws 16.

Figure 3:
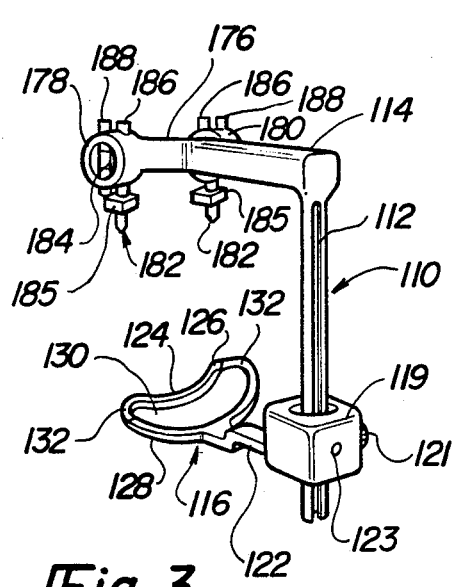
FIG. 3 is a perspective side view of a drill guide assembly having a plane guide in position.

With reference now to FIGS. 3 and 4, aligning and drilling of the respective bores for implantation of the staple through the jaw bone 10, presents a significant problem in the accurate implantation of the compression staple 10. The mounting axis of the staple must be as close as possible to normal to a lateral axis of the prosthesis. The flat mating surface 44 must be accurately positioned on the inferior border 46 of the jaw to permit abutting contact with the upper surface 24 of the base plate 22 of the staple. The flat mating surface 44 provides support against displacement of the staple and permits compressive attachment of the base plate to the jaw 12 by way of the lag screws 14. Additionally, the plurality of throughbores 40 and plurality of blind bores 43 must be properly aligned so as not to have the staple bind or otherwise damage the jaw bone or to cause subsequent later problems and injury.

It is, therefore, of primary importance to properly locate and form the mating surface for the staple. Additionally, the respective bores must be drilled such as to be in perfect alignment with and corresponding to the spacing of the transosteal pins 28 and circular apertures 30 of the staple. It is, likewise, primarily essential that the bores drilled through the jaw bone be accurately located with respect to the jaw bone centerline and inwardly of the open nerve centers of the jaw bone.

Figure 6:
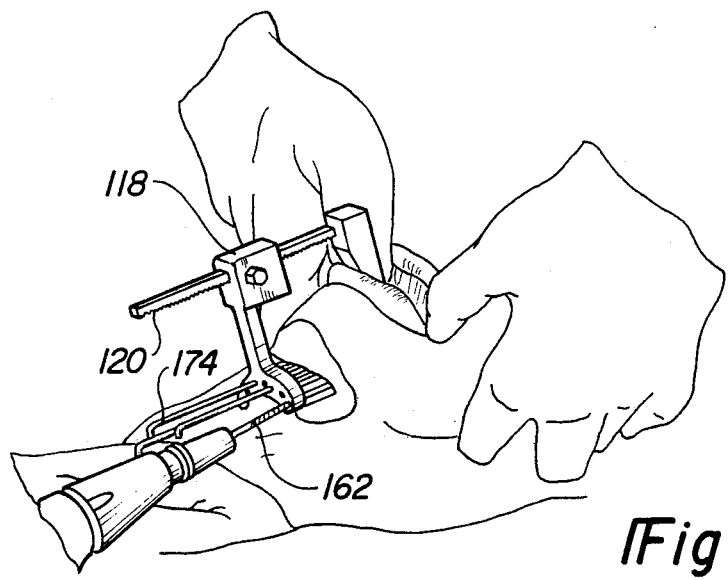
FIG. 6 is a perspective view of the drill guide in position as used during a drilling operation in the implant procedure.
Figure 10:
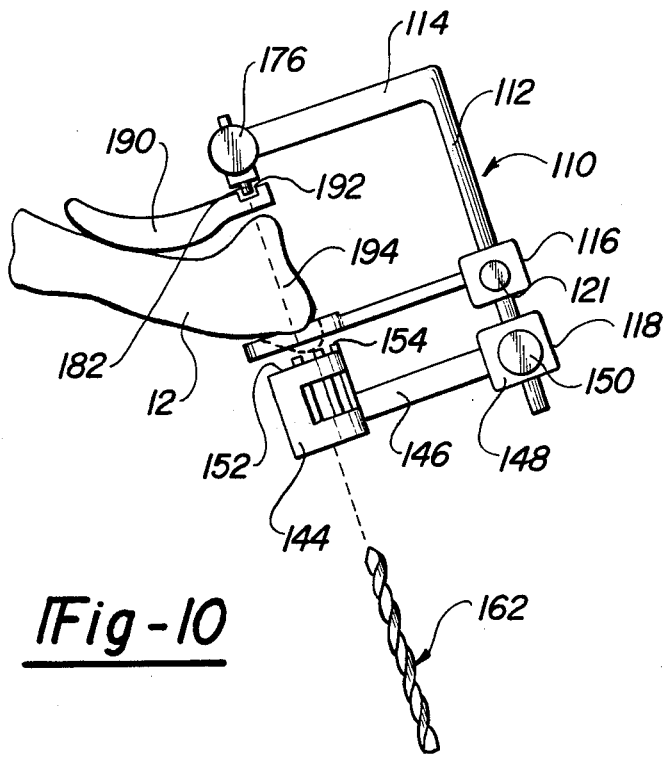
FIG. 10 is a side view of the drill guide assembly in position for use with a plane guide and a drilling chamber.

For this purpose there is provided the present improved drill guide assembly, generally indicated at 110, as shown in FIG. 10. The drill guide assembly 110 consists of an elongated post 112 which at an upper end stationarily supports an upper arm 114 and removably supports a plane guide 116 and a drilling chamber 118 which are slidable along the post 112 towards or away from the upper arm 114. Both the plane guide 116 and drilling chamber 118 are movable and removable along the post 112. As disclosed in my prior U.S. Pat. No. 3,664,022, which is incorporated by reference herein, the post 112 has an inner surface 120 (FIG. 6) having back teeth which are engaged by a gear (not shown) suitably supported for roation within an enlarged rear portion 119 (FIG. 3) of the plane guide.

Extending from the enlarged rear portion 119 of the plane guide, as shown in FIG. 3, is a bar 122 supporting a loop 124 having an upper surface 126 and lower surface 128. The loop 124 forms a curvilinear aperture 130 conforming to the shape of the base plate 22 of the four pin staple, however, having dimensions slightly greater than the staple. The aperture 130 is formed to accept a lower protruding portion of the jaw within. A curved surface 132 is disposed along the upper surface 126 at each end of the loop 124. The curved surface 132 has a radius to accept the radius of the jaw bone in order that the plane guide 116 can be closely aligned on the jaw bone. The lower surface 128 of the plane guide forms a flat guiding surface 134 for a burring tool 136 to permit reduction of any portion of the lower jaw protruding through the aperture, as shown in FIG. 4. The guiding surface 134 extends on a plane normal to the longitudinal axis of the post 112 and mounting axis 194 to permit formation of the mating surface 44 on the jaw for accepting the upper surface 24 of the base plate 22 of the staple.

The burring tool 136 has a bit 138 having a smooth tip portion 140 and a knurled grinding portion 142 extending inwardly from the tip portion 140. A smooth cylindrical portion 143 extends inwardly from the grinding portion 143. The grinding surface has an axial length less than the width of the aperture 130 of the plane guide 116. The tip portion 140 and cylindrical portion 143 are adapted to ride along the guiding surface 134 of the loop to facilitate grinding of the bone to produce the flat mating surface 44 for the staple as shown in FIG. 4.

The plane guide 116 may be moved into position for alignment of the mounting axis or grinding and may be removed as desired. When the plane guide is in position, a set screw 123 may be threaded in the enlarged rear portion 119 to contact the post 112 to lock the plane guide in position.

Figure 5:
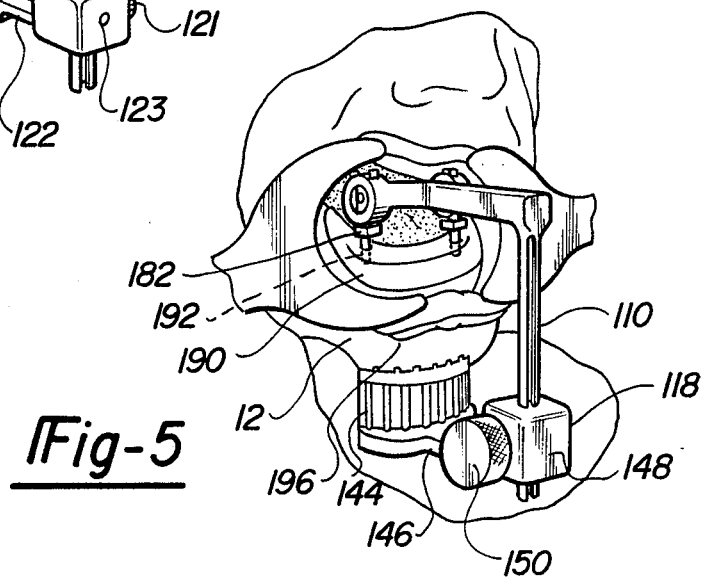
FIG. 5 is a perspective view of the drill guide assembly with a drilling chamber in position for drilling.
Figure 12:
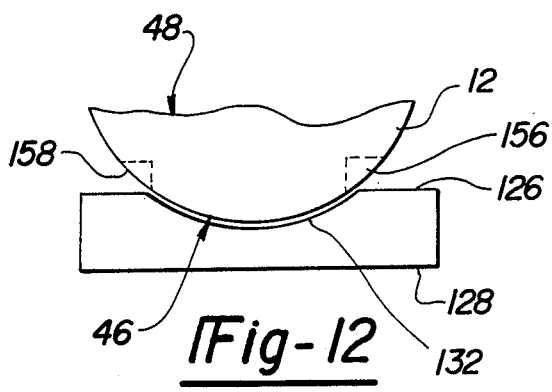
FIG. 12 is a side view of an end of a loop of the plane guide in position on the inferior border.

As shown in FIG. 5, the drilling chamber 118 is movably supported along the post 112 by a rear portion assembly 148 in the same manner as disclosed above for the plane guide 116. A hand wheel 150 acts to move a gear (not shown) for movement of the drilling chamber along the post. An arm 146 extends from the rear portion assembly of the drilling chamber 118 in a direction normal to the axis of the post 112 to support a transverse curvilinear shaped barrel 144. The barrel 144 has a flat surface 152 extending on a plane parallel with the guiding surface 134 of the plane guide 116. A plurality of teeth 154 extend outwardly from a peripheral edge of the flat surface 152 of the barrel 144 of the drilling chamber. The plurality of teeth 154 extend to engage the jaw bone and lock the barrel 144 of the drilling chamber in place against the mating surface 44 formed with the plane guide 116. In the event the flat surface 152 of the drilling chamber cannot be positioned flush against the mating surface 44 because of abutment of the plurality of teeth against the jaw bone, an additional labial groove 156 (FIG. 12) with a radius corresponding to the radius of the peripheral edge supporting the plurality of teeth of the drilling chamber may be formed on the jaw to accept the teeth. In some cases, a slight lingual groove 158 may be necessary. The plurality of teeth 154 are adapted to bite into the lower surface of the jaw bone in order to lock the barrel in position and to prevent slipping or movement during the drilling operation.

The barrel 144 of the drilling chamber, as shown in FIG. 2, has seven apertures 160 adapted to receive a plurality of sleeves 164 for guiding the bit 162 of a drill for drilling holes in the mandibular jaw bone 10 for implantation of the staple. The seven apertures correspond to positions 1 to 7 of the four pin staple 20 shown in FIG. 2. The seven apertures, thus, correspond in spacing and number to the spacing and number of transosteal pins 28 and circular openings 30 of the four pin staple 20 and are adapted for drilling the bores associated with the positions 1-7. The barrel is also adapted to drill the bores for the two pin staple since positions 2 through 6 for the two pin staple correspond in position to positions 2 through 6 of the four pin staple.

Figure 7:
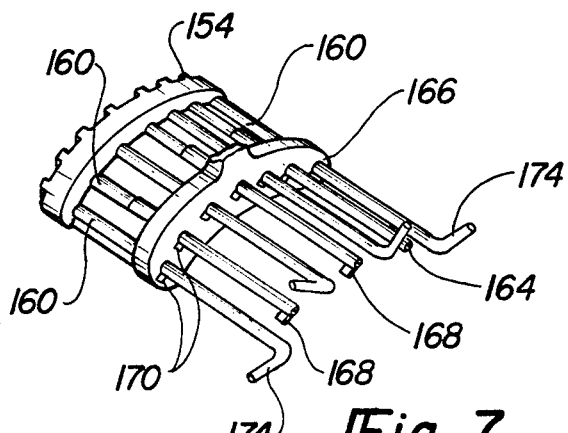
FIG. 7 is a perspective view of the drilling chamber for the drill guide.
Figure 13:
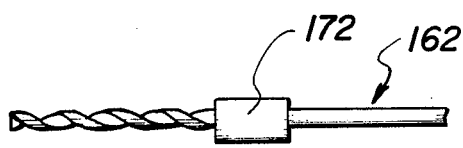
FIG. 13 is a top view of a drill bit for use with the drilling guide.

Each of the plurality of sleeves 164 has an outer diameter corresponding to the diameter of each aperture 160 extending through the barrel of the drilling chamber. Each sleeve has an inner diameter corresponding to the desired diameter of the bore required to be drilled. Thus, when drilling the plurality of throughbores for the transosteal pins, a sleeve having an inner diameter corresponding to a 7/64 drill bit is provided. Additionally, sleeves having an inner diameter corresponding to the drill bit sizes for the blind bores for the lag screws are provided. As shown in FIG. 7, on the outer surface at one end of each sleeve 164 is positioned an arm or key 168 to engage a keyway 170 formed on the lower surface 166 of the barrel of the drilling chamber to prevent movement or rotation of each sleeve when used for drilling. When drilling, a sleeve having the appropriate inner diameter is inserted in the designated position in the barrel. The inner diameter is selected in accordance with whether a throughbore is being drilled for a transosteal pin or a blind bore is being drilled for the lag screws. Thus, four sleeves having an appropriate inner diameter are positioned in positions 1, 3, 5 and 7 for drilling the throughbores for the four pin staple. The sleeves are locked in position by the key and keyways. As shown in FIG. 10, an appropriately sized drill bit 162 is then inserted through the sleeve for drilling the throughbores. As shown in FIG. 13, the depth of the hole is controlled by a stop 172 affixed to the drill bit 162, thereby establishing the depth to be drilled. In drilling the blind bores for the lag screws, one set of sleeves must be used to drill the blind bore for the threads of the lag screw and a separate set of sleeves having a larger inner diameter are used for countersinking the cylindrical shaped portion of the lag screw.

The curvilinear shape of the barrel 144 of the drill guide is adapted to be received within the aperture 130 of the plane guide 160, if so desired, for use during alignment of the mounting axis 194. The curvilinear shape of the barrel corresponds to the curvilinear shape of the support plate of the staple. As seen in FIG. 7, the rear of the barrel is slotted from end to end, intersecting the apertures 160 to provide a lateral opening for access to each of the apertures for the plurality of sleeves 164.

As shown in FIG. 3, the front end of the upper arm 114 supports a yoke member 176 which extends transversely of the arm 114 to both sides thereof. Both outer ends of the yoke member are formed cylindrically at 178 and 180 and each outer end has a pair of pins having an inner pin 186 and an outer pin 188 to support two director rods 182 for extension downwardly towards the barrel of the drilling chamber. The pins 188 are yieldably supported for relative longitudinal up or down movement at opposite ends of a centrally pivoted see-saw lever 184 which extends longitudinally through the yoke member 176 and is pivotally secured therein at its center. As disclosed in my prior patent, when one pin is moved upwardly, the other opposite director rod is forced to move downwardly and vice-versa. This pivotal reciprocating arrangement of the pins 186 and 188 and director rods 185 is provided to accomodate for unevenness in the jaw bone thickness. The pair of inner pins 186 define an inner position and the outer pins 188 define an outer position for the director rods. Both director rods 182 are threadably mounted to the pins by an attachment member 185 to either the inner position or the outer position pins depending on which staple is being used. The inner and outer positions permit offsetting the director rods from the end of the drill bit when drilling the throughbores for the transosteal pins. The inner position of pins 186 is used when drilling for implantation of the four pin staple and the outer position of pins 188 is used for drilling during implantation of the two pin staple.

In use of the present improved mandibular drill guide assembly for application of the improved staple 10 or 20, the initial step includes making a plaster mold of the arcuate front portion of the mandibular lower jaw of the patient and a clear plastic template 190 (FIG. 10) corresponding to the gum portion of the denture. The template 190 is then bored at two spaced locations to form apertures 192 at a predetermined distance such as to be clear of and between the exposed nerve centers on both sides of the jaw bone. The spacing between the apertures 192 in the template 190 is intended to correspond to the actual spacing of the two director rods 182. The spacing of the apertures 192 is selected to correspond to either the inner position pins 186 or outer position pins 188 of the yoke. The mounting alignment of the staple can be selected and checked for accuracy by attaching the director rods 182 to the apertures 192 of the template which is positioned on the jaw.

With more particular reference to FIG. 10, the drill guide assembly 110 is then aligned with the plane guide 116 in position on the lower side of the jaw bone of the patient after first pulling back the tissue around the portions of the jaw bone. The plane guide 116 of the drill guide assembly 110 is adjusted such as to abut against the underside of the curved front portion of the jaw bone to accept a portion of the jaw bone in the aperture 130 of the loop 124.

The drill guide assembly 110 is aligned on the jaw bone with the apertures 160 as close to parallel as possible with the axis of compression of the jaw. The alignment is limited by the shape of the jaw bone. That is, the mounting axis must extend through sufficient portion of the jaw bone to support the transosteal pins and provide sufficient bone to accept the lag screws 14. It has been found that the mounting axis may be generally within 5° to 10° of the axis of compression of the jaw. However, a portion of the inferior border of the jaw bone must be removed to form the mating surface 44 to provide a base for the compression of the lag screws and prevent displacement of the staple.

After alignment, the protruding portion of the jaw bone is ground flat to provide the mating surface 44 by utilizing the guide surface 134 of the plane guide 116 and the burring tool as described above and shown in FIG. 4.

The barrel of the drill guide is then positioned to determine whether there is sufficient clearance for the teeth around the mating surface. In the event there is insufficient clearance, additional grooves 156 and 158 may be formed with a grinding tool as set forth above and shown in FIG. 12. After sufficient clearance is provided to align the flat surface 152 of the barrel 144 with the mating surface 44, the teeth 156 of the barrel, in attached position, bite into the jaw bone to prevent lateral or rotational displacement of the drill guide assembly during the drilling operation.

After the drilling chamber 118 has been attached to the lower mandibular jaw bone 12 of the patient as described above, a drill, indicated at 162 in FIG. 6, of the proper size is selected to first drill the throughbores 40 in the jaw bone which are adapted to receive the transosteal pins 28 of the staple. As set forth above, a set of sleeves of proper inner diameter is slid into each aperture 160 of the barrel 144 in the positions 1, 3, 5 and 7 on the four pin staple and positions 2 and 6 for the two pin staple.

After the first throughbore 40 is drilled through the mandibular jaw bone by guidance of the drill through an appropriate sleeve in the drilling chamber, a rod 174 of proper diameter is inserted through the aperture 160 and through the throughbore 40 which has been drilled through the jaw bone for the purpose of further anchoring the drill guide assembly 110 in its previously located position on the jaw bone to avoid accidental displacement during drilling of the remainder of the throughbores. The second throughbore is then similarly drilled through the jaw bone by utilization of the opposite outer end aperture 160 in the barrel of the drilling chamber and another rod 174 of proper diameter is inserted through the aperture 160 and the drilled throughbore 40 in the jaw bone whereby the drill guide assembly 110 is now anchored at two spaced points to positively prevent any displacement.

Thereafter, the remainder of the throughbores 40 are drilled, if necessary. The blind bores 42 are drilled on the jaw bone 10 for insertion of the lag screws 14 of the staple, utilizing a drill of different size and a sleeve having a corresponding inner diameter. The sleeve is inserted in apertures corresponding to positions 2, 4 and 6. The drill bit has the stop 172 at a proper distance from its pointed tip, as is commonly known in drilling blind bores. Thus, as previously explained, the blind bores 42 for the lag screws of the staple do not extend all the way through the mandibular jaw bone 12. Employing a drill of slightly larger diameter and a sleeve having an appropriate inner diameter, another set of blind bores is formed coaxially with the first set of blind bores for counter-sinking the lag screws 16.

In the case of the mandibular jaw having an anterior mandible too small to allow proper drilling of holes for pins at positions 1 and 7, a two transosteal pin staple 10 is required. The two pin staple 10, as shown in FIG. 1, has a transosteal pin at the 2 and 6 positions and the shorter threaded pin 132 in position 4. Two circular openings 30 for two lag screws 14 are positioned at the 3 and 5 positions.

The four transosteal pin staple has 28% more interface with bone for stabilization and fixation and is necessary for a fixed bridge attachment. Thus, the four pin staple should be used whenever possible. Additionally, the two pin staple provides insufficient stabilization from the two sleeve nuts 16 to provide a support for a fixed implant.

With all the drilling complete, the drilling guide assembly is removed. The staple is then implanted by pushing the transosteal pins 28 through the proper throughbores 40 in the jaw. The staple is positioned with the upper surface 24 of the base plate 22 in abutting contact with the mating surface 44 of the jaw. In order to properly position the staple, an implant driver (not shown) may be used to tap the plate against the mating surface 44. The staple may be malleted by a series of blows against the implant driver to completely seat against the mating surface on the inferior border of the mandible.

With the staple 20 firmly seated, the lag screws 14 are inserted into the blind bores 44 previously drilled. A Spline screwdriver (not shown) may be used to drive the self-tapping lag screws into position. After the staple has been compressively screwed together, the transosteal pins are cut to approximately 3 mm above the gingiva with a pin cutter (not shown). The transosteal pins are then re-threaded with a thread cutter to remove any burrs from the pin.

As set forth above, the trephine 58 is used to cut tissue away from the threads of the transosteal pin 28 through the gingiva. The cutting trephine has a sleeve 198 having a blade end 200 extending from a knurled handle 202. The sleeve is open to extend over the top of the transosteal pin while the blade end of the trephine has a sharpened edge to cut the tissue and enlarge the throughbore 40 extending through the gingiva to accept the sleeve of the sleeve nut. The handle 202 is gripped by hand to force the trephine along the transosteal pin.

The crest leveler tool 60 is used to level the top surface of the bone beneath the gingiva around the transosteal pin to permit the sleeve of the nut 16 to extend the proper distance through the gingiva. The crest leveler tool 60 has a sleeve 204 having an inner diameter to accept the transosteal pin and a serrated edge portion 206 at the end of the sleeve 204. A handle 208 extending from the sleeve is used to turn the crest tool to level the bone through engagement with the serrated edge 206.

The sleeve nut 16 is then threaded into position with the bottom of the sleeve contacting the level top of the jaw bone. The sleeve nut 16 is then locked into position by threading the plug into a top of the sleeve nut with a spline wrench, as set forth above.

The day after surgery, the patient may be referred to a general dentist to have holes drilled in the old denture so that no material touches the sleeve nuts. After healing, a fixed or removable appliance may be fabricated for mounting on the compression staple. If a four pin transosteal staple is used, a fixed appliance 212 may be formed and mounted, as shown in FIG. 14. In this manner, a compression staple may be affixed to the jaw to provide a tight support for a fixed appliance.

I claim:

1. A staple assembly for implantation in a mandibular jaw for supporting a dental prosthesis; said staple assembly comprising:
    a staple having a base plate and a plurality of parallel threaded transosteal pins; said base plate having a flat upper surface and a lower surface adapted to flatly mate with a flat surface on the inferior border of said mandibular jaw, said base plate having at least two circular openings extending through said base plate, each of said plurality of transosteal pins of a length to extend through said mandibular jaw and having one end affixed to said base along a predetermined arc ascribed on said upper surface and having a free end extending through said mandibular jaw whereby said free ends are positioned in a predetermined parallel spaced apart relationship, and
    at least two self-tapping lag screw members having head portions, each of said at least two lag screw members adapted to extend through a respective one of said at least two openings in said base plate to threadably engage a bone portion of said mandibular jaw whereby said flat upper surface of said base plate is compressively mated with said flat surface of said inferior border of said mandibular jaw when said screw members are tightened and said head portions engage said lower surface of said base plate.

2. The staple assembly as claimed in claim 1 further comprising a plurality of threaded nuts, each of said plurality of nuts being threaded to a respective one of said plurality of threaded pins, each of said plurality of nuts having an elongated sleeve portion extending axially from a head portion of said nut, said sleeve portion having a predetermined length to extend through gingiva to contact said bone of said mandibular jaw, said plurality of nuts extending axially parallel to each other to support said dental prosthesis.

3. The staple assembly of claim 2 wherein said head portion of each of said plurality of nuts has a spherical surface adapted for accepting said dental prosthesis.

4. A drill guide assembly for use with a drill and a grinding apparatus for mandibular staples, said drill guide assembly adapted for positioning and drilling a plurality of throughbores and a plurality of blind bores in spaced apart parallel alignment with a mounting axis through a mandibular jaw with a drill bit, said drill guide assembly comprising:
    an elongated post having a pair of ends;
    a yoke member mounted to one of said pair of ends of said post for supporting said drill guide assembly in an upper position above said jaw;
    a plane guide detachably mounted to said post, said plane guide having a loop portion having a flat guide surface extending on a plane, said loop portion defining an aperture adapted for receiving a portion of said jaw with a protruding portion projecting beyond said guide surface within, whereby a planar mating surface may be formed on said jaw by grinding said projecting portion to extend along said plane, said planar mating surface extending normal to said mounting axis;

means for guiding said drill bit for forming a plurality of apertures in said jaw bone, said means for guiding being detachably mounted to said post.

5. The drill guide assembly of claim 4 wherein said means for guiding comprises a drilling chamber having a flat upper surface and a plurality of teeth extending from said upper surface for lockingly engaging said jaw whereby said drilling chamber is held in position with respect to said jaw for drilling to prevent displacement of said drill bit along said jaw.

6. The drill guide assembly of claim 5 wherein said aperture of said loop portion has a curvilinear shape.

7. The drill guide assembly of claim 6 wherein said drilling chamber has a curvilinear barrel portion adapted to be received within said aperture of said loop portion of said plane guide.

8. The drill guide assembly of claim 7 wherein said means for drilling further comprises:
a first plurality of drilling sleeves adapted for insertion into said drilling chamber, each of said first plurality of drilling sleeves having a first predetermined inner diameter;
a second plurality of drilling sleeves adapted for insertion into said drilling chamber, each of said second plurality of drilling sleeves having a second predetermined inner diameter; and
means for locking said first and second plurality of drilling sleeves from rotation in said drilling chamber.

9. The drill guide assembly of claim 8, wherein said means for locking comprises:
a plurality of keyways formed in said barrel portion of said drilling chamber, and wherein each of said first and second pluralities of drilling sleeves has a key portion extending from an end to be received in said keyway of said barrel portion.

10. The drill guide assembly of claim 4 further comprising a pair of director rods mounted to said yoke member, said yoke member having two pairs of positioning pins, one pair of said two pairs of positioning pins defining an inner position for said director rods and an other of said two pair of positioning pins defining an outer position adapted for accepting said pair of director rods.

11. A method for implanting a staple having a plurality of transosteal pins and a base in a jaw, said method comprising:
determining a mounting axis for said staple,
positioning a loop of a plane guide about a portion of said jaw bone,
grinding a portion of bone of said jaw with a tool in conformance with said plane guide to produce a flat surface normal to said mounting axis,
drilling a plurality of throughbores and a plurality of blind bores in said jaw parallel with said axis of alignment of said staple,
inserting said plurality of transosteal pins into said plurality of throughbores in said jaw,
threading each of a plurality of compression screws through apertures in said base of said staple into a respective one of said plurality of blind bores to mount said staple to said jaw bone in compression.

12. The method of claim 11 further comprising the step of covering the thread of said plurality of transosteal pins extending through gingiva of the jaw with a sleeve of a nut threaded onto each of said plurality of transosteal pins.

13. The method of claim 11 further comprising the step of forming a notch about said flat mating surface produced on said jaw for accepting a plurality of teeth extending from a drilling chamber of said plane guide to lock said drilling chamber in place for drilling.

14. The method of claim 11 further comprising the step of cutting a portion of gingiva with a trephine for accepting said sleeve of said nut.

15. The method of claim 11 further comprising the step of leveling a portion of bone about said throughbore with a tool for mounting said nut.

* * * * *

UNITED STATES PATENT AND TRADEMARK OFFICE
CERTIFICATE OF CORRECTION

PATENT NO. : 4,917,604
DATED : April 17, 1990
INVENTOR(S) : Irwin Small

It is certified that error appears in the above-identified patent and that said Letters Patent is hereby corrected as shown below:

Column 5, line 1, after "22", insert --as indicated in FIG. 2. The transosteal pins and base plate 22--.

Signed and Sealed this

Twentieth Day of August, 1991

Attest:

HARRY F. MANBECK, JR.

Attesting Officer

Commissioner of Patents and Trademarks